United States Patent [19]

Tazi et al.

[11] Patent Number: 4,948,848

[45] Date of Patent: * Aug. 14, 1990

[54] SOLUTION FEED, SLURRY POLYMERIZATION PROCESS FOR THE PRODUCTION OF COPOLYMERS OF MALEIC ANHYDRIDE AND AN ALKYL VINYL ETHER HAVING PREDETERMINED SPECIFIC VISCOSITIES

[75] Inventors: Mohammed Tazi, Wayne; Nikhil Kundel, Piscataway, both of N.J.

[73] Assignee: GAF Chemicals Corporation, Wayne, N.J.

[*] Notice: The portion of the term of this patent subsequent to Jul. 3, 2007 has been disclaimed.

[21] Appl. No.: 334,405

[22] Filed: Apr. 7, 1989

[51] Int. Cl.$^5$ .................. C08F 2/06; C08F 222/06; C08F 216/18; A61K 6/083

[52] U.S. Cl. .................................. 526/78; 526/79; 526/87; 526/208; 526/216; 526/271; 526/332; 523/120

[58] Field of Search .................. 526/78, 79, 87, 208, 526/216, 271, 332; 523/120

[56] References Cited

U.S. PATENT DOCUMENTS 2,694,698  11/1954  Grosser .................................. 526/77
3,178,395  4/1965  Muskat .................................. 526/79
3,956,244  5/1976  Carpenter et al. .................... 526/79

FOREIGN PATENT DOCUMENTS 310079  4/1989  European Pat. Off. .

*Primary Examiner*—Joseph L. Schofer
*Assistant Examiner*—Tom Weber
*Attorney, Agent, or Firm*—Walter Katz; Marilyn J. Maue; Joshua J. Ward

[57] ABSTRACT

What is described herein is a solution feed, slurry precipitation polymerization process for making copolymers of maleic anhydride and an alkyl vinyl ether within a predetermined viscosity range.

The process of the invention is characterized by precharging a large excess of the alkyl vinyl ether in a reactor, feeding maleic anhydride dissolved in a minimum amount of an organic solvent into the precharged reactor, and polymerizing the monomers in the presence of a free radical initiator. The copolymer product then appears as a pumpable slurry in the reaction medium. The slurry is discharged from the reactor and the desired copolymer is obtained therefrom as a fine, white powder having specific viscosities in the range of about 1.5–6.0, and preferably about 2.6–3.5.

16 Claims, No Drawings

SOLUTION FEED, SLURRY POLYMERIZATION PROCESS FOR THE PRODUCTION OF COPOLYMERS OF MALEIC ANHYDRIDE AND AN ALKYL VINYL ETHER HAVING PREDETERMINED SPECIFIC VISCOSITIES

BACKGROUND OF THE INVENTION

1. Field of the Invention

This invention relates to a process for making copolymers of maleic anhydride and an alkyl vinyl ether, and, particularly, to a solution feed, slurry polymerization process for making high viscosity copolymers within a predetermined viscosity range.

2. Description of the Prior Art

Several methods are known for preparing copolymers of maleic anhydride (MA) and an alkyl vinyl ether, e.g. methyl vinyl ether (MVE). For example, it is known:

(1) To react a charge of MA dissolved in a large excess of MVE in a pressure reactor. However, this method is disadvantageous because considerable heat is evolved during the polymerization, and, under these process conditions, it is difficult to remove this heat effectively. Furthermore, homopolymers of MVE can form during the polymerization, and this by-product reduces the overall viscosity of the product obtained.

(2) To control the heat released during the reaction, molten MA has been fed into a reactor precharged with a large excess of MVE. Unfortunately, in this method, the reaction rate is strongly dependent upon the degree of agitation provided in the reactor, which parameter is difficult to regulate. As a result, the viscosity of the copolymers obtained cannot be controlled effectively.

(3) Another available method requires feeding molten MA into a reactor precharged with MA dissolved in a solvent. This method avoids the necessity of a large excess of MVE; however, as in method (2) above, it is very difficult to monitor the feed rate of molten MA into the reactor, and, accordingly, localized polymerization occurs with the resultant formation of undesirable by-products.

(4) MVE also can be fed into a reactor precharged with MA dissolved in a solvent. However, this method does not provide high viscosity copolymers within a predetermined viscosity range.

OBJECTS OF THE INVENTION

Accordingly, it is an object of this invention to provide an improved process for preparing copolymers of maleic anhydride and an alkyl vinyl ether.

Another object is to provide such copolymer products within a predetermined viscosity range.

A further object herein is to provide a solution feed, slurry precipitation polymerization process for making MA-MVE copolymers which avoids the difficulties and limitations associated with prior art processes.

Specifically, it is intended herein to avoid feeding molten MA; of generating an excessive amount of heat internally; of requiring a large amount of solvent; and of process conditions which promote localized polymerization leading to formation of undesirable by-products.

Still another object of this invention is to provide a process capable of producing copolymers of MA-MVE as a pumpable slurry from which fine, white copolymer powders can be obtained which have a predetermined viscosity in the range of about 1.0 to 6.0, preferably about 2.6 to 3.5, as measured in a 1% solution of 2-butanone.

These and other objects of the invention will be made apparent from the following description of the invention.

SUMMARY OF THE INVENTION

What is described herein is a solution feed, slurry precipitation polymerization process for making copolymers of maleic anhydride and an alkyl vinyl ether within a predetermined viscosity range.

The process of the invention is characterized by precharging a large excess of the alkyl vinyl ether in a reactor, feeding maleic anhydride dissolved in a minimum amount of an organic solvent into the precharged reactor, and polymerizing the monomers in the presence of a free radical initiator. The copolymer product then appears as a pumpable slurry in the reaction medium. The slurry is discharged from the reactor and the desired copolymer is obtained therefrom as a fine, white powder having specific viscosities in the range of about 1.5–6.0, and preferably about 2.6–3.5.

DETAILED DESCRIPTION OF THE INVENTION

In accordance with the invention, the process is carried out in the presence of a large excess of MVE, which dissolves the MA monomer, and a minimum amount of solvent. The copolymer product, however, is insoluble in the reaction medium, and, accordingly, it forms a pumpable slurry, comprising the product in excess MVE.

Preferred organic solvents for the MA reactant include ethyl acetate and acetone. The MA: ethyl acetate weight ratio in the feed solution suitably is about 1:1 to 1:4, and, preferably, about 1:1 to 1:0.5. For acetone, this ratio suitably is about 1:0.5 to 1:4 and preferably about 1:0.5 to 1:1.

The resultant MA:MVE weight ratio in the reaction mixture containing ethyl acetate suitably is about 1:3 to 1:10, and preferably about 1:4. In acetone, this ratio is about 1:3 to 1:10; and the preferred ratio is about 1:5.

The polymerization reaction is carried out at a temperature of about 45°–85° C., preferably at about 50°–60° C., and at the pressure of the reactants.

Polymerization is effected in the presence of a free radical initiator selected from peroxy esters, diacyl peroxides, dialkyl peroxides, hydroperoxy esters, azo nitriles, and the like. Representative initiator compounds include t-butylperoxy pivalate, benzoyl peroxide, lauryl peroxide, decanoyl peroxide, and azo bis-butyronitrile. t-Butylperoxy pivalate is a preferred catalyst.

The initiator generally is introduced at a level of about 0.1–2% by weight based on the amount of MA present in the reaction, and, preferably at about 0.2–0.4%.

The process of the invention may be carried out sequentially by precharging a reactor with a large excess of a $C_1$–$C_5$ alkyl vinyl ether, preferably methyl vinyl ether, heating the ether to the reaction temperature; introducing the initiator, and then feeding a solution of MA in a minimum amount of a suitable organic solvent continuously over a period of about 2–6 hours, preferably about 4 hours. Polymerization is effected in the solution of MA dissolved in the large excess of MVE.

The reaction product then is held for at least about an hour at the reaction temperature to complete the polymerization. At this point, a slurry is formed comprising copolymer solid in excess MVE and solvent.

Excess MVE then is vented off and collected, or, preferably, prior to venting, a non-solvent for the copolymer, such as toluene, is added to the slurry product to maintain the solid polymer in slurry form. At his point, the slurry is discharged and dried. The copolymer product is a fine white powder.

Under these process conditions, the copolymer product has a specific viscosity in the range of about 1.5–6.0, and, under preferred process conditions, it has a predetermined, controllable specific viscosity in the range of about 2.6–3.5, as determined by measurements in a 1% solution of 2-butanone.

High viscosity copolymers are obtained by the process of the invention because propagation of the copolymer by reaction between monomers forms large molecules, which immediately precipitate out of solution. These propagation reactions are favored over other propagation reactions involving the solvent because the solvent is present in only small amounts in the reaction medium. Therefore, the polymerization reaction rate is dependent only upon the reactivity ratio of the monomers present, not on the concentration of the feed solution.

Accordingly, selection of suitable MA: solvent and MA:MVE weight ratios will predetermine the viscosity of the resultant copolymer. For example, when a large excess of MVE and a minimum amount solvent is present, for a given amount of MA, very high specific viscosities can be obtained within the preferred range of 2.6–3.5. Moreover, if desired, specific viscosities in the range of about 1.0–2.6 can be made by reducing the amount of MVE present and increasing the amount of, for example, ethyl acetate used in the process.

The invention will be illustrated by the following examples.

EXAMPLE 1

A 1-liter pressure reactor was precharged with 50 g. of MVE and the monomer reactant was heated to 56° C. during 0.5 hours. Then 0.56 g. of t-butylperoxy pivalate (Pennwalt Corp., a 75% solution in mineral oil) was added.

A solution of 37.5 g. of MA in 56.25 g. of ethyl acetate then was fed into the reactor continuously during 4 hours. The mixture was then held at 56° C. for about an hour.

The MA: ethyl acetate weight ratio present in the feed solution was 1:1.5; the MA: MVE weight ratio in the reaction mixture was 1:4.0; and the initiator level was 1.5%, based on the weight of MA present.

During the polymerization, a slurry of the copolymer product in the reaction mixture appeared. Then 250 ml. of toluene was added to the slurry reaction product to maintain the copolymer in slurry form. Excess MVE was vented off and the slurry is discharged. The copolymer was recovered as a fine white powder by drying.

The specific viscosity of the copolymer obtained was 3.0, as measured in 2-butanone (1% solution).

EXAMPLE 2

A 1-liter pressure reactor was precharged with 187.5 g. of MVE and heated to 58° C. during 0.5 hr. Then 0.15 g. of t-butylperoxy pivalate was added.

A solution of 37.5 g. of MA in 8.75 g. of acetone then was fed into the rector continuously during 3 hours. and the mixture was held at 58° C. for an hour.

The MA: acetone weight ratio in the feed solution was 1:0.5; the MA: MVE weight ratio in the reaction mixture was 1:5; and the initiator level was 0.4% based on the weight of MA present.

A slurry of the copolymer in the reaction mixture formed during the polymerization. Then 250 ml. of toluene was added, excess MVE vented off and the slurry is discharged. The copolymer was obtained as a fine, white powder, by drying.

The specific viscosity of the copolymer product was 3.46, as measured in water (1% solution).

The copolymer product of the invention is particularly useful in denture additives where specific viscosities in the range obtained herein are preferred.

While the invention has been described with particular reference to certain preferred embodiments, it will be understood that changes and modifications may be made which are within the skill of the art. Accordingly, it is intended to be bound only by the appended claims, in which:

What is claimed is:

1. A solution feed, slurry polymerization process for making copolymer powders of maleic anhydride and a $C_1$–$C_5$ alkyl vinyl ether havingt a predetermined high specific viscosity suitable for use in denture adhesives which comprises:
   (a) precharging a reactor with a substantial excess of a $C_1$–$C_5$ alkyl vinyl ether,
   (b) feeding a solution of maleic anhydride dissolved in a minimum amount of an organic solvent selected from ethyl acetate and acetone into the precharged reactor,
   (c) copolymerizing said reactants at a temperature of about 45–85° C. in the presence of a free radical initiator, to form a pumpable slurry of the copolymer in the reaction medium, and
   (d) recovering the copolymer product therefrom as a fine white powder having a specific viscosity of about 2.6 to about 3.5 measured as a 1% solution in 2-butanone at 25° C., and,
   when the solvent is ethyl acetate, the maleic anhydride to ethyl acetate weight ratio in the feed solution is about 1:1 to 1:4 and the maleic anhydride to alkyl vinyl ether ratio in the reaction mixture is about 1:3 to 1:10; and
   when the solvent is acetone, the maleic anhydride to acetone weight ratio is about 1:0.5 to 1:4 and the maleic anhydride to alkyl vinyl ether weight ratio is about 1:3 to 1:10.

2. A process according to claim 1 wherein the alkyl vinyl ether is methyl vinyl ether.

3. A process according to claim 1 wherein the initiator is present in an amount of about 0.1 to 2% by weight, based on maleic anhydride.

4. A process according to claim 1 wherein the maleic anhydride to solvent weight ratio is about 1:1 to 1:1.5, and the maleic anhydride to alkyl vinyl ether weight ratio is about 1:4.

5. A process according to claim 1 wherein the polymerization temperature is about 50°–60° C.

6. A process according to claim 1 wherein the initiator is selected from peroxy esters, diacyl peroxides, dialkyl peroxides, hydroperoxy esters and azo nitrile.

7. A process according to claim 6 wherein the initiator is a peroxy ester.

8. A process according to claim 7 wherein the is t-butylperoxy pivalate.

9. A process according to claim 3 wherein the initiator is present in an amount of about 0.2 to 0.4%.

10. A process according to claim 1 wherein the solution of maleic anhydride in an organic solvent is introduced into the reactor continuously over a period of about 2-6 hours.

11. A process according to claim 10 wherein said solution is introduced over 4 hours, followed by a hold at the reaction temperature of at least one hour.

12. A process according to claim 1 wherein a non-solvent for the copolymer is introduced into the slurry reaction product to maintain the product in slurry form while removing excess alkyl vinyl ether.

13. A process according to claim 12 wherein the pumpable slurry is discharged and the product recovered by drying.

14. A process according to claim 1 wherein the polymerization reaction rate is dependent substantially on the relative reactivities of the monomer reactants only.

15. A process according to claim 1 wherein the polymerization reaction is carried at the pressure of the reactants in the reaction mixture.

16. A process according to claim 2 wherein the solvent is ethyl acetate, the maleic anhydride to ethyl acetate weight ratio is about 1:1.5, and the maleic anhydride to methyl vinyl ether weight ratio is about 1:4.0.

* * * * *